(12) United States Patent
Meyer

(10) Patent No.: US 10,080,501 B2
(45) Date of Patent: Sep. 25, 2018

(54) INTRAVASCULAR DEVICES, SYSTEMS, AND METHODS

(71) Applicant: Volcano Corporation, San Diego, CA (US)

(72) Inventor: Doug Meyer, Folsom, CA (US)

(73) Assignee: VOLCANO CORPORATION, San Diego, CA (US)

( * ) Notice: Subject to any disclaimer, the term of this patent is extended or adjusted under 35 U.S.C. 154(b) by 921 days.

(21) Appl. No.: 14/513,025

(22) Filed: Oct. 13, 2014

(65) Prior Publication Data

US 2015/0105654 A1    Apr. 16, 2015

Related U.S. Application Data

(60) Provisional application No. 61/890,547, filed on Oct. 14, 2013.

(51) Int. Cl.

| | |
|---|---|
| *A61B 5/0215* | (2006.01) |
| *A61B 5/01* | (2006.01) |
| *A61B 17/00* | (2006.01) |
| *A61B 8/12* | (2006.01) |
| *A61B 5/042* | (2006.01) |
| *A61B 1/05* | (2006.01) |
| *A61B 5/00* | (2006.01) |
| *A61B 1/04* | (2006.01) |
| *A61B 1/313* | (2006.01) |

(52) U.S. Cl.
CPC .............. *A61B 5/0215* (2013.01); *A61B 1/04* (2013.01); *A61B 1/3137* (2013.01); *A61B 5/0066* (2013.01); *A61B 5/01* (2013.01); *A61B 8/12* (2013.01); *A61B 2562/225* (2013.01)

(58) Field of Classification Search
CPC .......... A61B 17/22; A61B 2017/00106; A61B 2017/22051; A61B 2017/220272; A61B 8/0833
See application file for complete search history.

(56) References Cited

U.S. PATENT DOCUMENTS

| 5,377,685 A | * | 1/1995 | Kazi | ........................ | A61B 8/12 |
| | | | | | 600/463 |
| 5,545,200 A | | 8/1996 | West | | |
| | | (Continued) | | | |

OTHER PUBLICATIONS

International Searching Authority/United States Patent Office, "Notification of Transmittal of the International Search Report and the Written Opinion of the International Searching Authority, or the Declaration," for PCT/US2014/060264, dated Jan. 26, 2015, 16 pages.

*Primary Examiner* — Baisakhi Roy

(57) ABSTRACT

Intravascular devices and systems include a flexible elongate member having a component configured to detect a physiological condition of a patient when the flexible elongate member is in a vasculature of the patient. The probe may also include a connector junction non-rotatably and permanently secured to the proximal portion of the flexible elongate member. The connector junction may be sized for grasping by a health care provider and for rotation to rotate the flexible elongate member when the flexible elongate member is in a vasculature of the patient. The connector junction may include a slack chamber to accommodate slack in a conductor that may be utilized when the flexible elongate member is introduced through tortious vasculature.

22 Claims, 7 Drawing Sheets

(56) References Cited

U.S. PATENT DOCUMENTS

| | | | |
|---|---|---|---|
| 6,241,744 B1* | 6/2001 | Imran | A61B 8/0833 |
| | | | 128/898 |
| 2007/0118038 A1 | 5/2007 | Bodecker | |
| 2009/0076375 A1 | 3/2009 | Maschke | |
| 2009/0299195 A1* | 12/2009 | Muller | A61B 5/0062 |
| | | | 600/466 |
| 2010/0168732 A1 | 7/2010 | Podhajsky et al. | |
| 2011/0178413 A1* | 7/2011 | Schmitt | A61B 5/0066 |
| | | | 600/478 |
| 2012/0143294 A1 | 6/2012 | Clark et al. | |
| 2012/0172703 A1 | 7/2012 | Esguerra et al. | |
| 2012/0238857 A1* | 9/2012 | Wong | A61B 3/16 |
| | | | 600/398 |
| 2013/0237864 A1 | 9/2013 | Mazar et al. | |

* cited by examiner

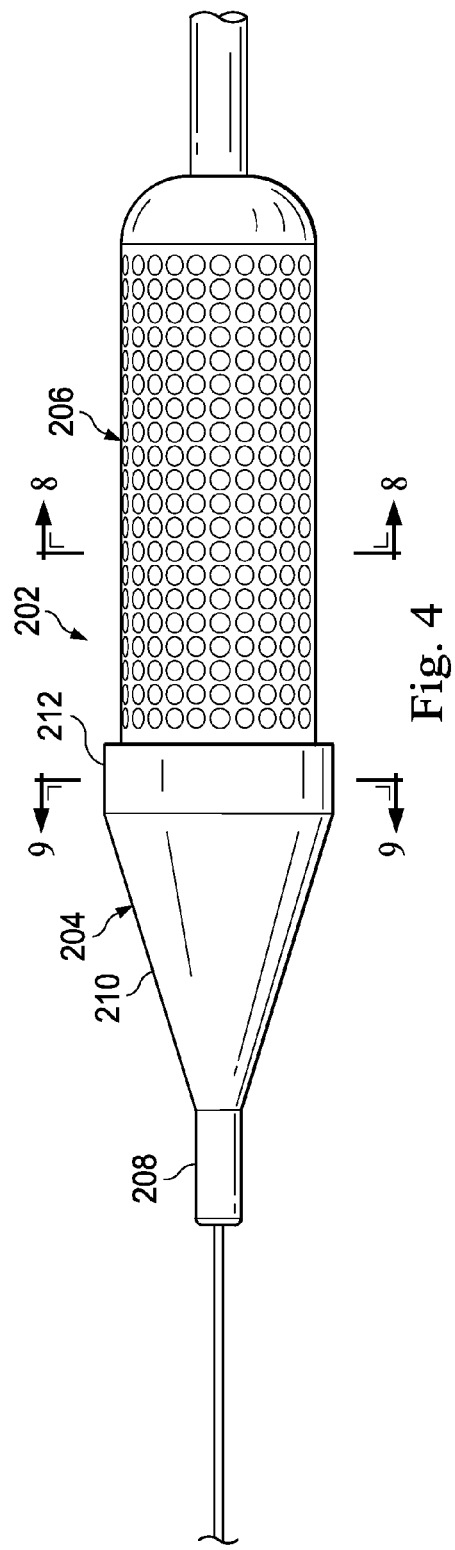
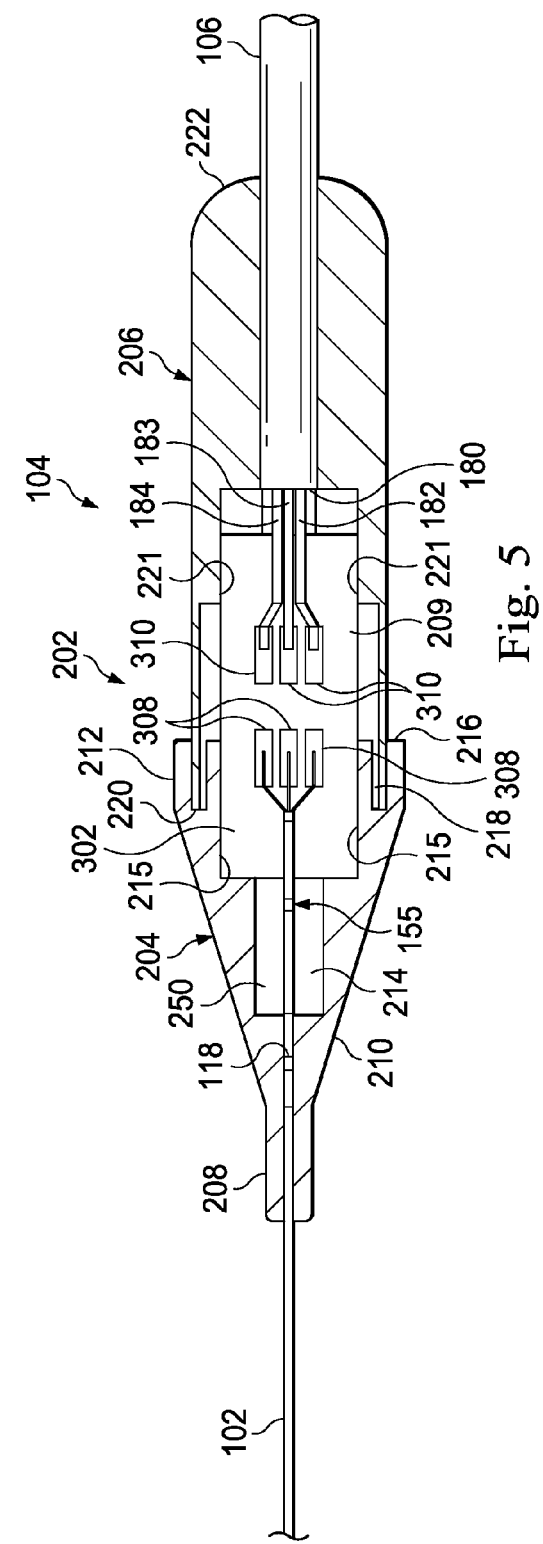

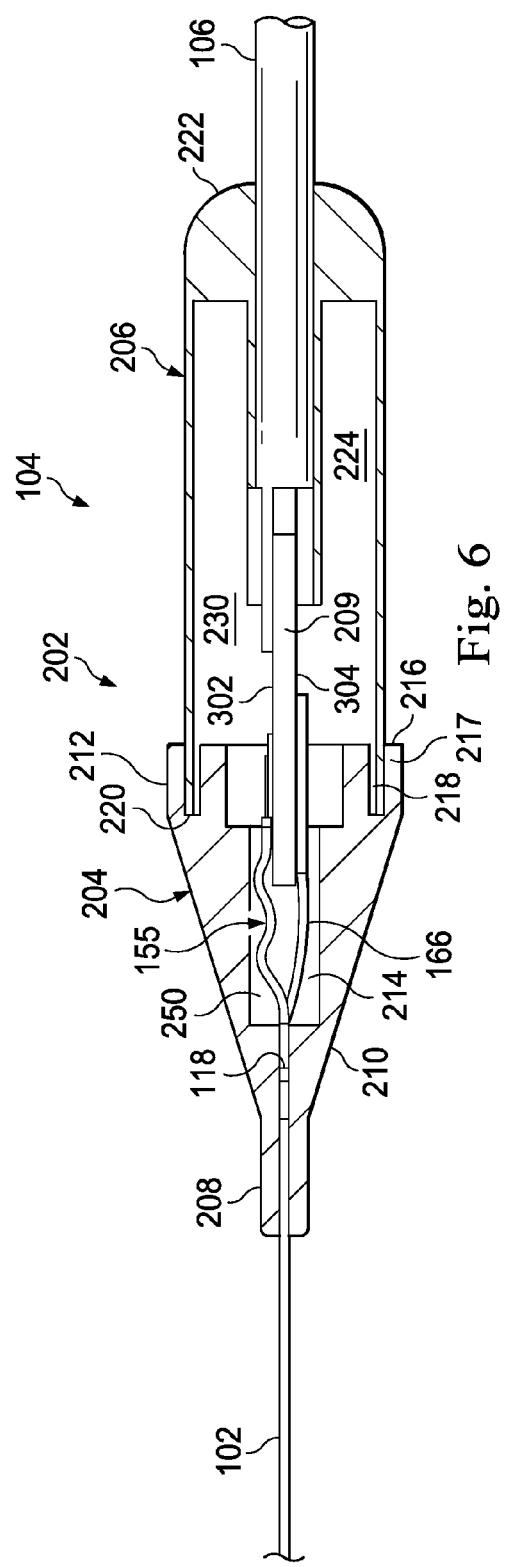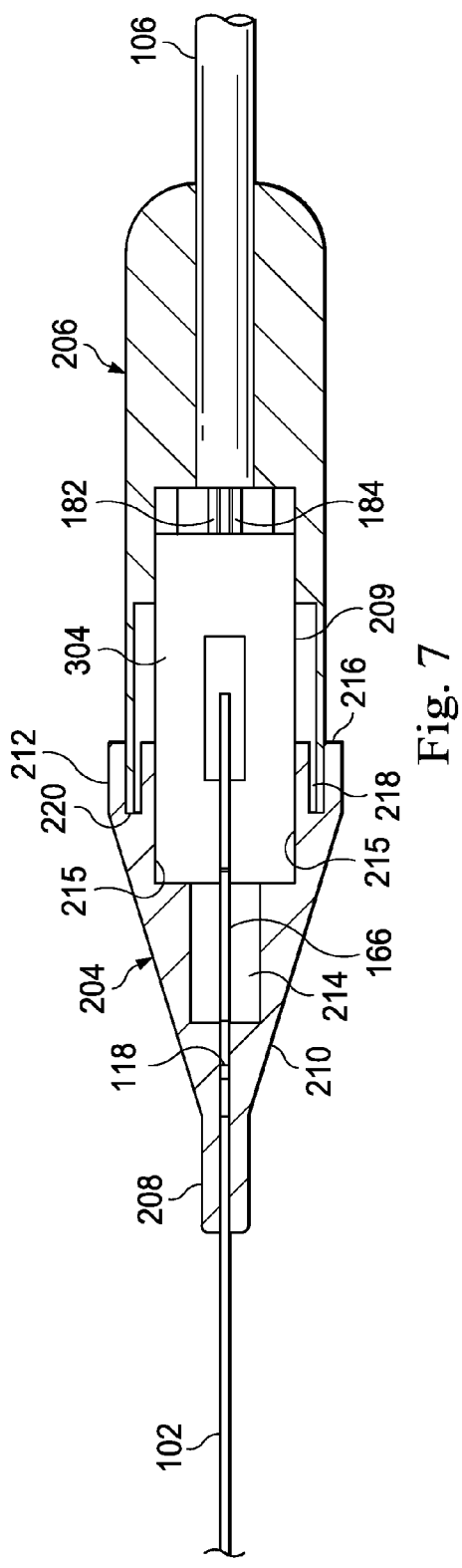

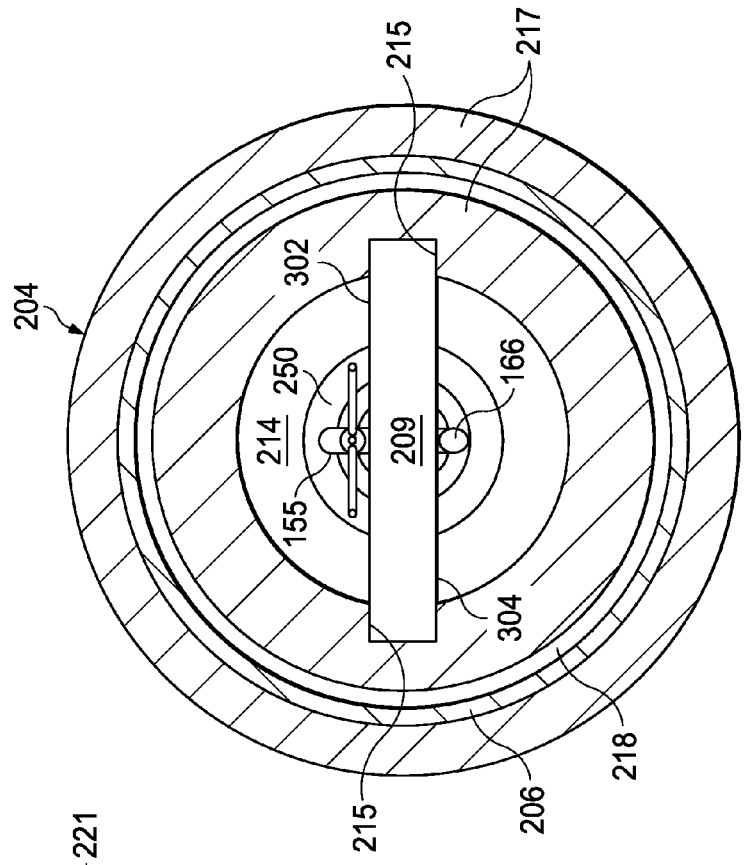
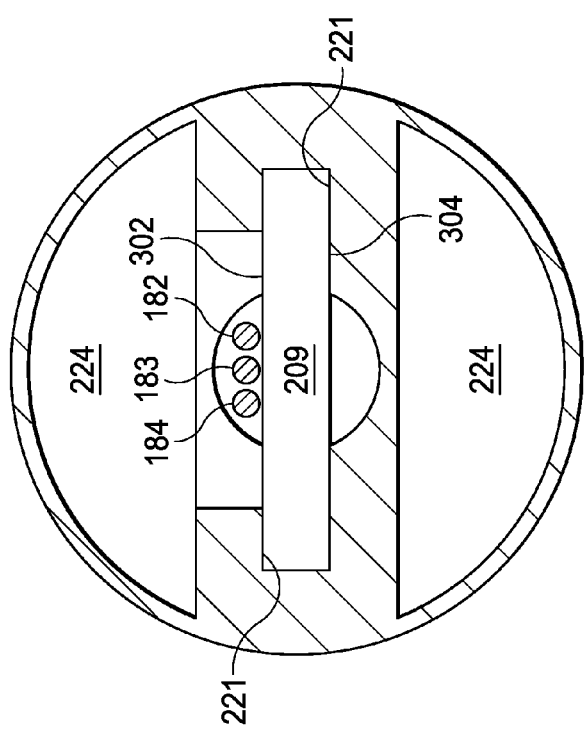
Fig. 9
Fig. 8

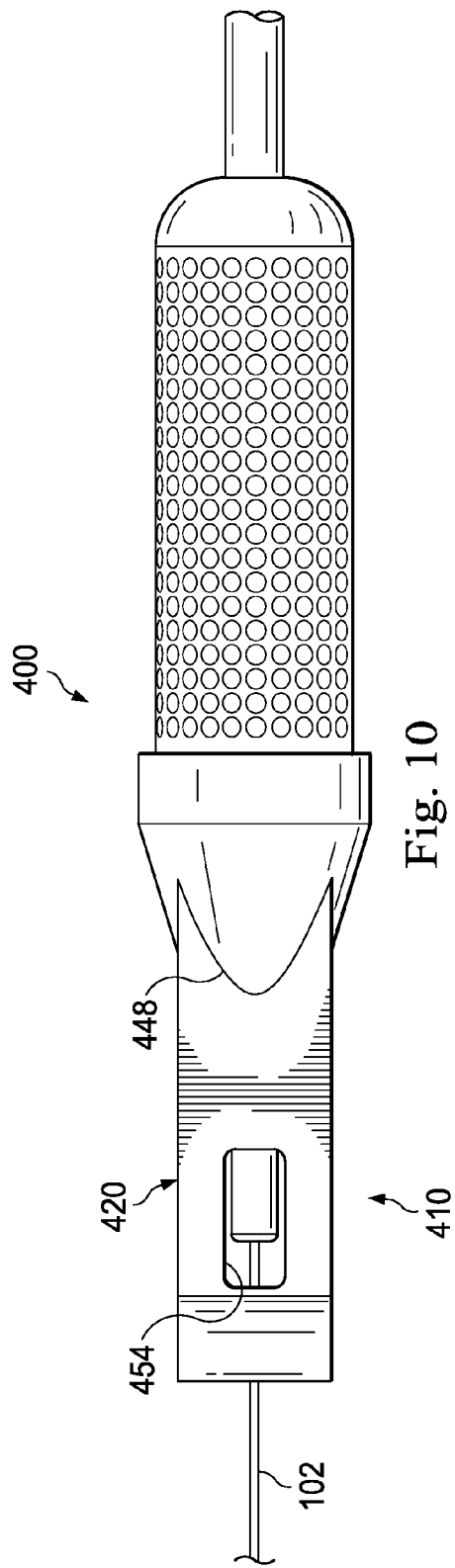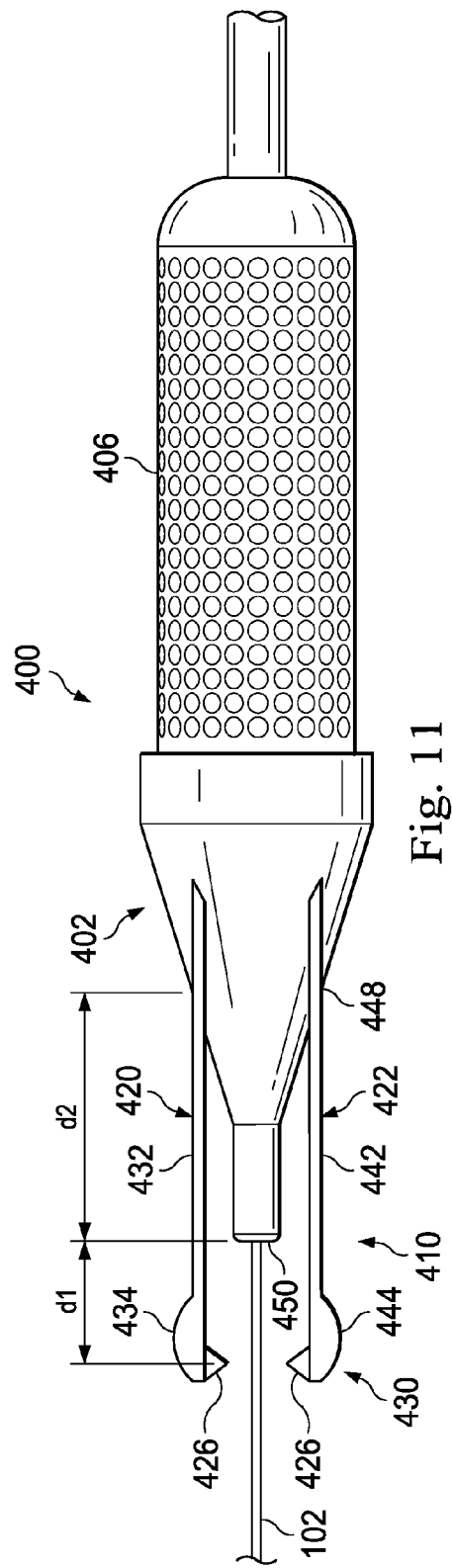

INTRAVASCULAR DEVICES, SYSTEMS, AND METHODS

CROSS-REFERENCE TO RELATED APPLICATION

The present application claims the benefit of the filing date of U.S. Provisional Application No. 61/890,547 filed Oct. 14, 2013. The entire disclosure of this provisional application is incorporated herein by this reference.

TECHNICAL FIELD

The present disclosure relates to intravascular devices, systems, and methods. In some embodiments, the intravascular devices are intravascular probes that include one or more electronic, optical, or electro-optical components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

Often intravascular catheters and guidewires are utilized to measure the pressure within the blood vessel, visualize the inner lumen of the blood vessel, and/or otherwise obtain data related to the blood vessel. Catheters containing pressure sensors, imaging elements, and/or other electronic, optical, or electro-optical components suffer from larger diameter bodies that can make passing through tortious vascualtorure more challenging, and may be too large to safely pass beyond some regions of stenosis. Guidewires containing pressure sensors, imaging elements, and/or other electronic, optical, or electro-optical components can have a higher incidence of electrical problems since they typically include fragile electrical connections that are disconnected and reconnected to accommodate catheters introduced over the guidewire. These fragile electrical connections often include conductor bands that enable the guidewire to rotate relative to a proximal connector while maintaining an electrical connection. However, these conductor bands are costly from a materials cost and a labor cost. Further, these connections may not provide the desired level of consistency and predictability.

In addition, because of their extremely small diameter, typically in the range of about 0.25 mm to 1.5 mm, current guidewires typically require an attachable torque device for manipulation of the guidewire. Attaching and detaching the torque device can be tedious and time consuming.

Accordingly, there remains a need for improved intravascular devices, systems, and methods that include one or more electronic, optical, or electro-optical components.

SUMMARY

Embodiments of the present disclosure are directed to intravascular devices, systems, and methods.

In an exemplary aspect, the present disclosure is directed to an intravascular probe that includes a flexible elongate member configured to be introduced into vasculature of a patient. The flexible elongate member may include a proximal portion and a distal portion. The distal portion may include a component thereon configured to detect a physiological condition of a patient when the flexible elongate member is in a vasculature of the patient. The flexible elongate member may comprise a core wire and a communication pathway extending at least partially along the core wire, the conductor being in communication with the component and extending to the proximal portion. The probe may also include a communication element configured to communicate signals representative of the detected physiological condition to a system, and may include a connector junction non-rotatably and permanently secured to the proximal portion of the flexible elongate member. The connector junction may be sized for grasping by a health care provider and for rotation to rotate the flexible elongate member when the flexible elongate member is in a vasculature of the patient. The connector junction may connect the conductor in the flexible elongate member to the communication element to convey signals relating to the detected physiological condition to a system.

In an aspect, the connector junction comprises a chamber configured to accommodate flexing of the conductor as slack in the conductor. In an aspect, the conductor comprises a loop as the slack in the conductor, the loop being disposed in the chamber. In an aspect, the connector junction includes a connector chamber and a circuit board disposed in the connector chamber, the conductor being in communication with the circuit board. In an aspect, the communication element is a cable extending from the connector junction. In an aspect, the conductor comprises at least three separate signal carrying wires. In an aspect, the housing is bonded to the proximal portion of the flexible elongate member with an adhesive. In an aspect, the component is a pressure sensor. In an aspect, the flexible elongate member comprises a first coil disposed distal of the components and comprises a second coil disposed proximal of the component, the first and second distal coils providing rigidity to the distal portion of the flexible elongate member. In an aspect, the flexible elongate member comprises component housing, the component being disposed in the component housing. In an aspect, the distal portion has a diameter of less than about 0.37 mm. In an aspect, the intravascular probe includes a cutting tool on the connector junction configured to permanently sever the flexible elongate member for removal of the connector junction in a manner that a balloon or stent catheter may be introduced to vasculature over the remaining flexible elongate portion. In an aspect, the flexible elongate member has a length between about 1300 and 4000 mm.

In another exemplary aspect, the present disclosure is directed to an intravascular probe including a flexible elongate member configured to be introduced into vasculature of a patient, where the flexible elongate member has a proximal portion and a distal portion. The distal portion includes a pressure sensor thereon configured to detect vascular pressures of a patient when the flexible elongate member is in a vasculature of the patient. The flexible elongate member may include a radiopaque coil disposed distal of the pressure sensor for visualization, and may include a conductor in electrical communication with the pressure sensor and extending to the proximal portion. The probe may also include a connector junction non-rotatably and permanently secured to the proximal portion of the flexible elongate member. The connector junction may include a housing, a hollow chamber in the housing, and a circuit board disposed in the hollow chamber. The conductor may be in electrical communication with the circuit board, and may be arranged to have slack in the hollow chamber to accommodate flexing and bending of the conductor when the flexible elongate member is manipulated through a patient's vasculature.

In another exemplary aspect, the present disclosure is directed to a method including providing a flexible elongate member configured to be introduced into vasculature of a patient, the flexible elongate member having a proximal portion and a distal portion, the distal portion including a component thereon configured to detect a physiological condition of a patient when the flexible elongate member is in a vasculature of the patient, the flexible elongate member comprising a core wire and a communication pathway extending at least partially along the core wire, the conductor being in communication with the component and extending to the proximal portion; and connecting the connector junction to the communication pathway; and permanently affixing a connector junction to the proximal portion of the flexible elongate member, the connector junction being sized for grasping by a health care provider and for rotation to rotate the flexible elongate member when the flexible elongate member is in a vasculature of the patient.

In an aspect, the method includes creating slack in the communication pathway to accommodate tension on the communication pathway applied as a result of inserting the flexible elongate member through tortious vasculature. In an aspect, the method includes looping the communication pathway to create the slack. In an aspect, the method includes forming a first coil distal of the component of the flexible elongate member and forming a second coil proximal of the component of the flexible elongate member. In an aspect, the method includes using the connector junction as a torque device during a medical procedure. In an aspect, connecting the connector junction includes soldering the conductor to circuitry maintained in the connector junction.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 4 is a diagrammatic side view of a connector junction according to an embodiment of the present disclosure.

FIG. 5 is a diagrammatic cross-sectional longitudinal view of the connector junction of FIG. 4 according to embodiment of the present disclosure.

FIG. 6 is a diagrammatic cross-sectional longitudinal view of the connector junction of FIG. 4 according to embodiment of the present disclosure.

FIG. 7 is a diagrammatic cross-sectional longitudinal view of the connector junction of FIG. 4 according to embodiment of the present disclosure.

FIG. 8 is a diagrammatic cross-sectional transverse view of the connector junction of FIG. 4 according to embodiment of the present disclosure.

FIG. 9 is a diagrammatic cross-sectional transverse view of the connector junction of FIG. 4 according to embodiment of the present disclosure.

FIG. 10 is a diagrammatic side view of a connector junction according to another embodiment of the present disclosure.

FIG. 11 is a diagrammatic side view of the connector junction of FIG. 10 according to another embodiment of the present disclosure.

DETAILED DESCRIPTION

Figure 1:
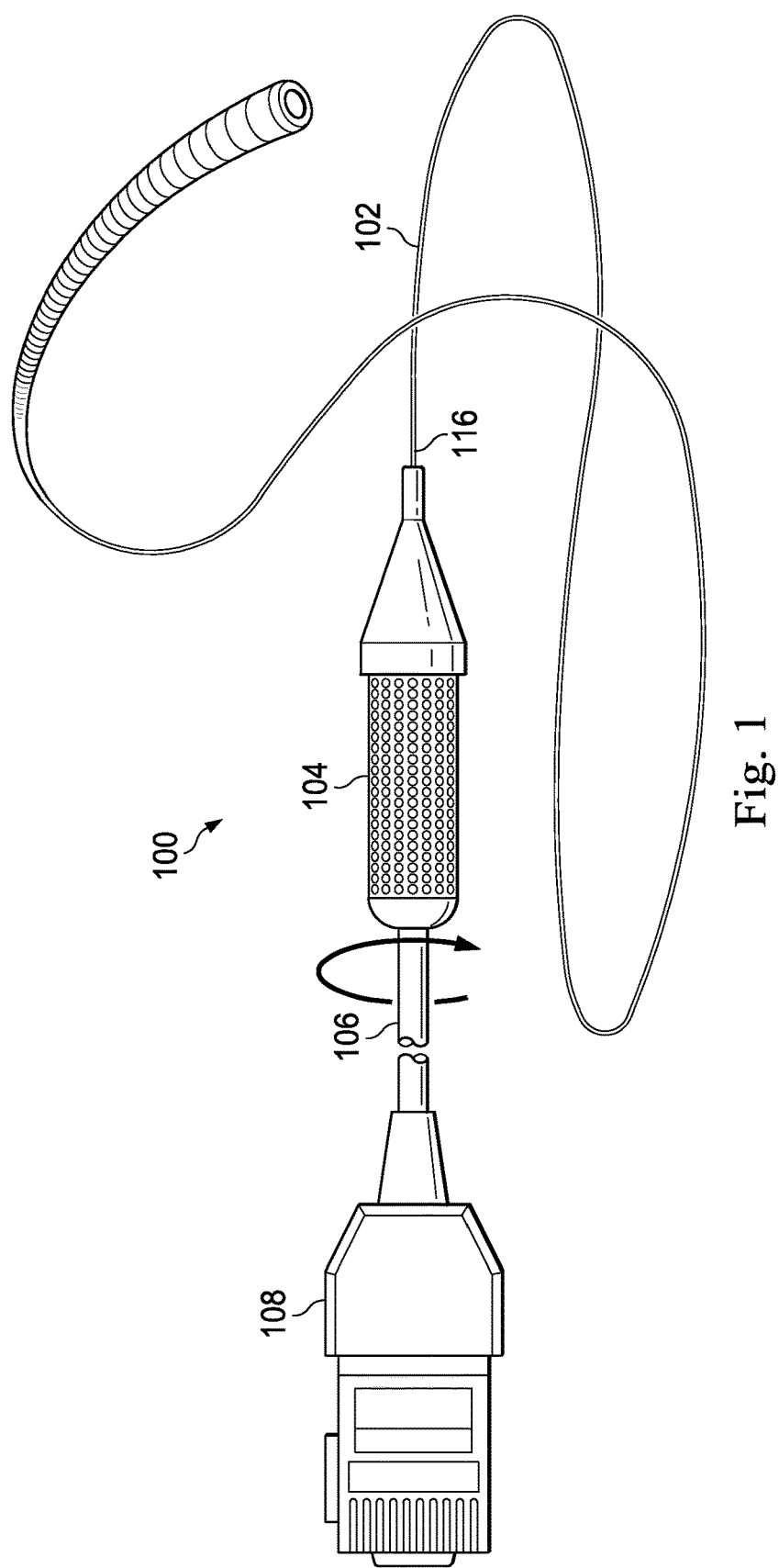
FIG. 1 is a diagrammatic stylized view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles.

The flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.035" (0.889 mm). As such, the flexible elongate members incorporating the electronic, optical, and/or electro-optical component(s) of the present application are suitable for use in a wide variety of lumens within a human patient besides those that are part of or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc., another element, as well as indirect connections where one or more elements are disposed between the connected elements.

"Secured" and variations thereof as used herein includes methods by which an element is directly secured to another element, such as being glued or otherwise fastened directly to, on, within, etc., another element, as well as indirect techniques of securing two elements together where one or more elements are disposed between the secured elements.

The present disclosure is directed to intravascular devices, such as probes, that are sized to pass through a patient's vasculature, including beyond some partial stenosis or other blockages that may limit passage of catheters, to monitor physiological condition of a patient. The devices described herein are more robust than prior devices because, despite their small diameter, they are formed with fixed and permanent sturdy electrical connections maintained in a connection junction. Because the connections are fixed and permanent, simple connection schemes may be used that reduce costs while increasing reliability. In addition to being protected by the connection junction, these connections are protected by configuring electrical conductors to include slack that reduces a chance of stress at the connectors from the probe as it is introduced through a vasculature. The connection junction is sized to be graspable and may be used as a permanent torque device that may be rotated to steer the intravascular device within the vasculature. Accordingly, the device disposed herein may be easier to operate, may be more reliable, and may be less expensive to create than prior devices. In addition, compared to guidewires, the device described herein may have a short length because other devices need not be loaded over it. Therefore, a health care provider may find it easier to handle than conventional guidewires or catheters.

Referring now to FIG. 1, shown therein is a portion of an intravascular device 100 according to an embodiment of the present disclosure. In that regard, the intravascular device 100 includes a flexible elongate member 102, a connector junction 104, a cable 106, and an electrical connector 108.

The elongate member 102 is described with reference to FIG. 2, and includes a distal portion 112 adjacent a distal end 114 and a proximal portion 116 adjacent a proximal end 118. A hypotube 119 forms all or part of the length of the elongate member 102. A component 120 is positioned along a component housing 122 within the distal portion 112 of the flexible elongate member 102 proximal of the distal end 114. Generally, the component 120 is representative of one or more electronic, optical, or electro-optical components. In that regard, the component 120 is a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device 100. In some instances, the component 120 is positioned less than 10 cm, less than 5 cm, or less than 3 cm from the distal end 114. In the exemplary embodiment shown in FIG. 2, the component 120 is positioned within the component housing 122 of the flexible elongate member 102. In that regard, the component housing 122 may be an element separate from a part of a main body, such as the hypotube 119, together forming a part of the flexible elongate member 102 in some instances. In other instances, the component housing 122 is integrally formed as a part of a main body or as a part of the hypotube 119 forming a part of the flexible elongate member 102.

In the exemplary embodiment shown, the flexible elongate member 102 also includes a distal coil 124 and a proximal coil 126 disposed adjacent to and on opposing sides of the component housing 122. In some embodiments, the distal and proximal coils 124, 126 are adjacent the component housing 120 by being disposed on or by forming a part of the component housing 122. The distal and proximal coils 124, 126 may be sized to extend around the distal portion 112 of the flexible elongate member 102, such that the flexible elongate member 102 has an outside diameter within the range of about, for example, 0.25 mm to 1.5 mm and is formed from a wire having a suitable diameter. Both larger and smaller sizes of coils and sizes of wires are contemplated.

In some embodiments, the distal and proximal coils 124, 126 are identically formed and are formed of a radiopaque material, such as a metal material. In some embodiments, the distal and proximal coils 124, 126 are formed of stainless steel. In some embodiments, the distal and proximal coils 124, 126 are formed of different materials, and one or both of these may be formed of a highly radiopaque material such as palladium or a tungsten platinum alloy. In some embodiments, the two coils have different axial lengths. For example, in some embodiments the proximal coil 126 may have a suitable length in the range of, for example, only of about 10-40 cm, while the distal coil 126 may have a length within the range of about 2-20 cm. Both longer and shorter coil lengths are contemplated. In some embodiments, the coils are the same lengths. In some embodiments, the component housing 122 has a suitable length in the range of, for example, 1-10 mm, although other lengths are contemplated. The use of the two coils 124, 126 on opposite ends of the component housing 122 provides a flexible floppy tip for the elongate member 102.

Communication pathways (not shown in FIG. 2) extend from the component 120 to the proximal end 118 and out of the elongate member 102 and provide communication between the component 120 and the connector junction 104 (FIG. 1). Generally, the communication pathways may be any number of electrical conductors, optical pathways, and/or combinations thereof that can extend along the length of the flexible elongate member 102 between the connector junction 104 and the component 120. In some instances, between one and ten electrical conductors and/or optical pathways extend along the length of the flexible elongate member 102 between the connector junction 104 and the component 120. For the sake of clarity and simplicity, the embodiments of the present disclosure described below include three electrical conductors as the communication pathways. However, it is understood that the total number of communication pathways and/or the number of electrical conductors and/or optical pathways is different in other embodiments. More specifically, the number of communication pathways and the number of electrical conductors and optical pathways extending along the length of the flexible elongate member 102 is determined by the desired functionality of the component 120 and the corresponding elements that define component 120 to provide such functionality.

Accordingly, information, such as image information, pressure information, or other detected information may be communicated from the connector junction 104 to the component 120 disposed at the distal portion 112 of the elongate member. Likewise, information, control, or actuation signals may be communicated to the component 120. Accordingly, in some embodiments, the flexible elongate member 102 is formed in part of a hypotube and the communication pathways extend from the component 120 at the distal portion 112, through the hypotube, to the proximal end 118. In some embodiments, the communication pathways extend from the proximal end 118 and out of the opening at the proximal end 118 into the connector junction 104 (FIG. 1).

While the total length of the flexible elongate member 102 can be any length, in some embodiments the total length is between about 1300 mm and about 4000 mm, while some specific embodiments have a length of 1400 mm, 1900 mm, and 3000 mm.

Figure 3:
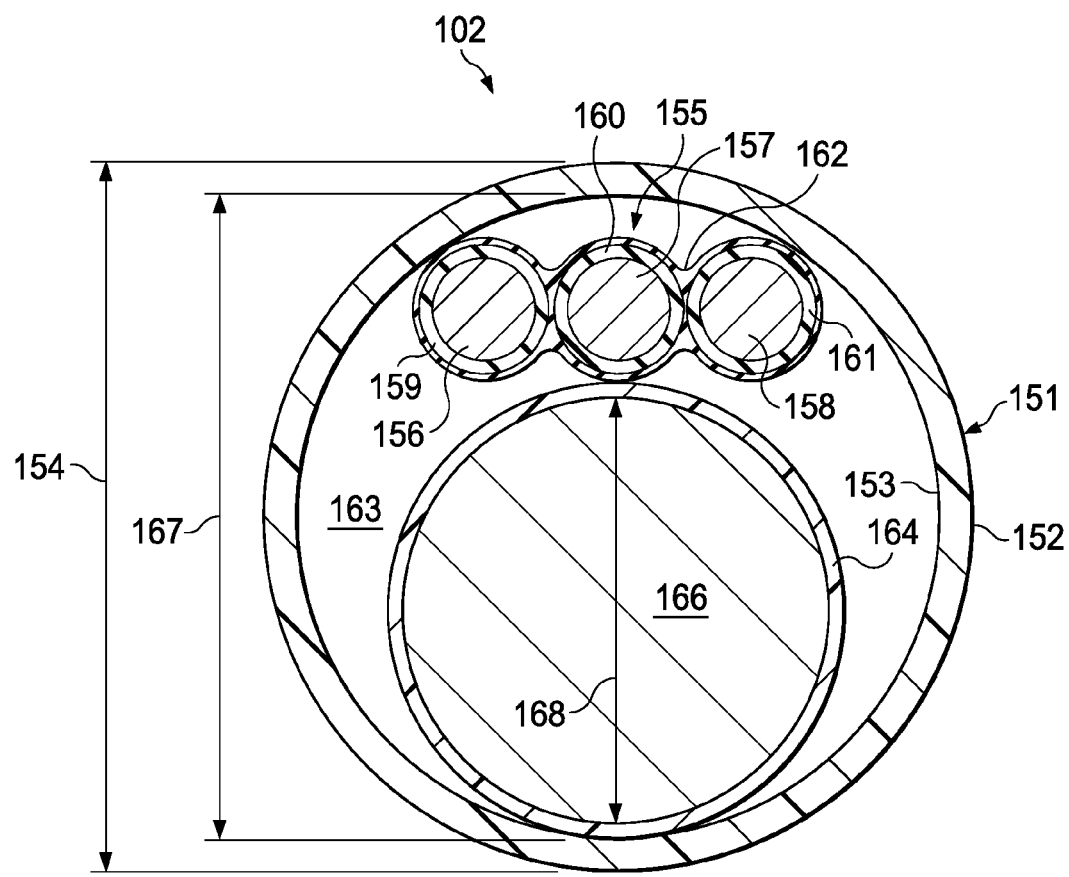
FIG. 3 is a diagrammatic cross-sectional view of a flexible elongated member according to an embodiment of the present disclosure.

FIG. 3 shows an exemplary cross-sectional view of the intravascular device 100 of the present disclosure illustrating an exemplary arrangement for extending communication pathways (e.g., electrical conductors and/or optical fibers) along the length of the flexible elongate member 102. In this example, for the sake of clarity and simplicity, the embodiment of FIG. 3 includes three electrical conductors. More specifically, the embodiment of FIG. 3 includes three electrical conductors arranged as a trifilar. Existing trifilars are typically formed by three individual copper wires each wrapped with a color coded insulation material. A final overcoat is put over all three wires to connect them together as a single trifilar component.

FIG. 3 shows a cross-sectional longitudinal view of the intravascular device 100 according to an embodiment of the present disclosure. The flexible elongate member 102 includes a main body 151 having an outer wall 152 defining an outer boundary of the flexible elongate member 102 and an inner wall 153 defining a lumen 163 for receiving additional components of the flexible elongate member 102 that will be discussed in greater detail below. In the illustrated embodiment the main body 151 has a circular cross-sectional profile with an outer diameter 154. Diameter 154 is between about 0.014" (0.3556 mm) and about 0.035" (0.889 mm) in some embodiments, with some particular embodiments having an outer diameter of approximately 0.014" (0.3556 mm) or approximately 0.035" (0.889 mm). In some embodiments, the main body 151 has a constant profile along all or a majority of its length. For example, where the main body 151 has a circular cross-sectional profile, as shown in FIG. 3, the various portions of the main body 151 maintain a constant outer diameter along all or a majority of the length of the flexible elongate member 102. In some embodiments, at least the portions of the main body 151 that are intended to be disposed within the patient have a constant profile (or at least tapered/gradual transitions between portions with different outer profiles) to avoid potential injury to the patient while advancing or axially rotating the flexible elongate member 102 through the patient. Further, it is recognized that the composition of the main body 151 changes along the length of the intravascular device in some instances. For example, in some embodiments the main body 151 transitions between one or more of a hypotube, a coil, a balloon, a polymer sleeve, and/or other structures and combinations thereof. The main body 151 maintains a constant profile across the transitions in some instances. In some embodiments, the main body 151 is a hypotube or other tube. In some embodiments, the main body 151 is or includes a polymer tubing with a conductive coil embedded therein.

The flexible elongate member 102 also includes a trifilar 155 disposed within the lumen of the main body 151 defined by the inner wall 153. In that regard, the trifilar 155 consists of three electrical conductors or wires 156, 157, and 158, which may be formed of any suitable conductive material including without limitation copper, copper alloys, silver, silver alloys, aluminum, and/or combinations thereof. Each of the wires 156, 157, and 158 is wrapped with an insulating layer 159, 160, and 161, respectively. Any suitable insulating layer may be utilized, including without limitation polyimide, polyurethane, nylon, polyethylene, polypropylene, silicone rubber, fluoropolymers, and/or combinations thereof. In some embodiments, the insulating layers 159, 160, and 161 are color coded or otherwise include markings or identifiers to facilitate identification of the corresponding conductors 156, 157, and 158. An overcoat layer 162 is formed over the three conductors 156, 157, and 158 and insulating layers 159, 160, and 161 to connect the conductors together as a single trifilar component 155. Layer 162 is formed of an insulating material in some instances. For example, in some embodiments, layer 162 is formed of one or more of polyurethane, polyethylene, polypropylene, silicone rubber, and/or combinations thereof. As shown, the trifilar 155 is positioned within the lumen 163 of the main body 151. In some instances, lumen 163 is open space. In other instances, the lumen 163 is partially or completely filled with a material. For example, in some instances a portion of the lumen 163 is filled with an adhesive, such as polyurethane, cyanoacrylate, acrylate, silicone, and/or combinations thereof, that is utilized to secure components of the flexible elongate member 102 together. Accordingly, in some instances, the material filling lumen 163 also surrounds a layer 164 and core wire 166. In that regard, the layer 164 is formed of polyethylene terephthalate (PET) in some instances and may extend along all, a portion, or none of the length of the core wire 166 (i.e., layer 164 is omitted in some instances). In some embodiments, the layer 164 has a thickness between about 0.0001" (0.0025 mm) and about 0.0005" (0.0127 mm). In some embodiments, the layer 164 is intermittently used along the length of the core wire 166 as an insulator at certain joints and/or to hold the trifilar 155 to the core wire 166.

As shown, the inner wall 153 of the main body 151 defines a lumen 163 having a diameter 167. The diameter 167 is dependent upon the outer diameter 154 of the main body 151 and the thickness of the main body between the outer wall 152 and the inner wall 153. As noted above, diameter 154 is between about 0.014" (0.3556 mm) and about 0.035" (0.889 mm) in some embodiments, with some particular embodiments having an outer diameter of approximately 0.014" (0.3556 mm) or approximately 0.035" (0.889 mm). Further, the thickness of the main body 151 between the outer and inner surfaces 152 and 153 is between about 0.0005" or 0.0157 mm and about 0.003" or 0.0762 mm. In some specific embodiments, the thickness is about 0.0254 mm, about 0.047 mm, or about 0.0508 mm. Based on the inner diameter 167, the size and orientation of the trifilar 155, and the thickness of layer 164, the core 166 has a maximum diameter 168.

In some instances, the arrangement of components shown in FIG. 3 limits the maximum outer diameter 168 of the core 166 to about 46% of the outer diameter 154 of the main body 151. For example, for a 0.014" outer diameter imaging device, the core diameter 168 is limited to about 0.0065".

Figure 2:
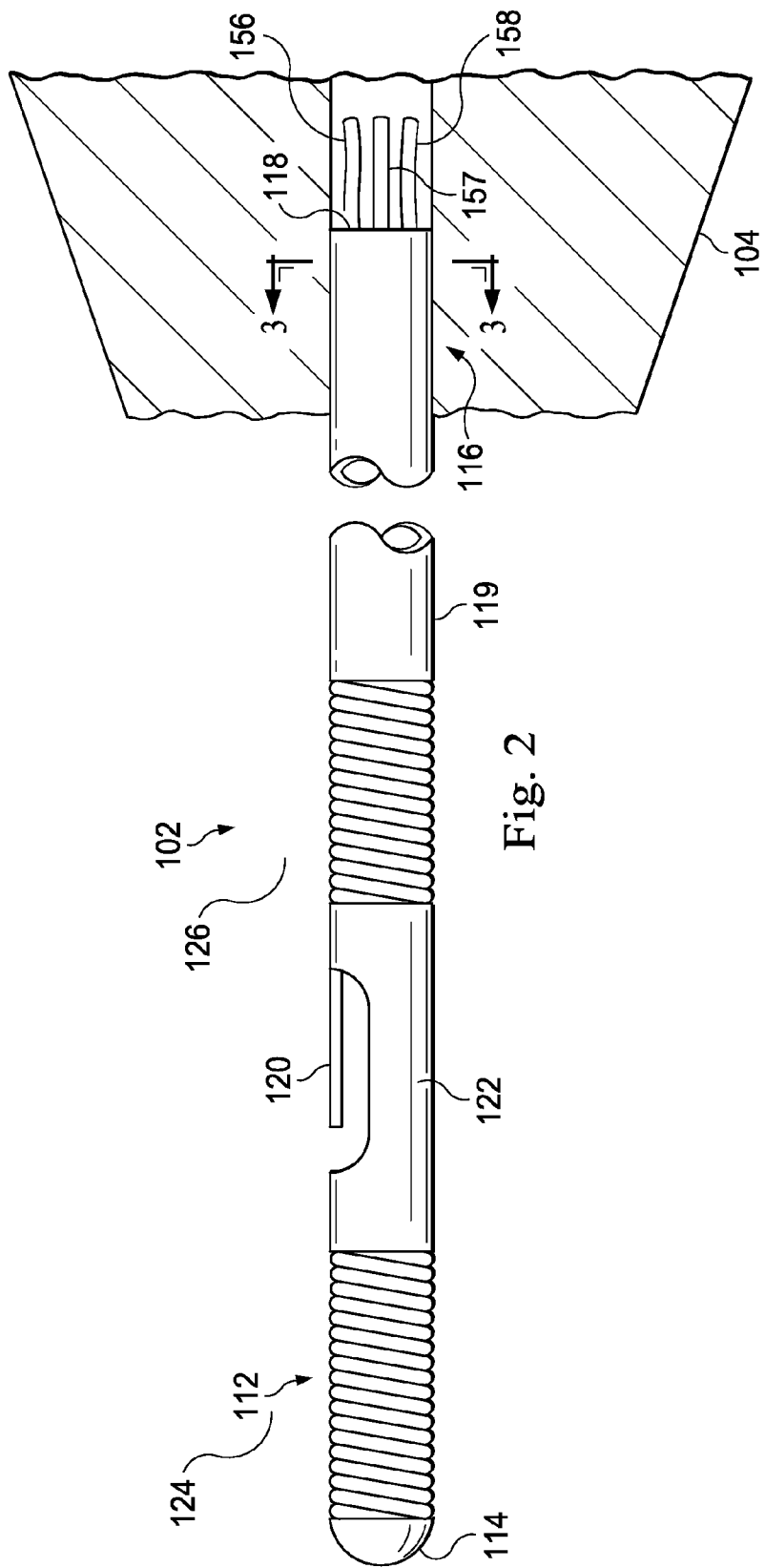
FIG. 2 is a diagrammatic side view of an intravascular device according to an embodiment of the present disclosure.

FIG. 2 shows a portion of the connector junction 104 disposed on or connected with the proximal portion 116 of the flexible elongate member 102. In some embodiments, the proximal end 118 is configured to be received within a portion the connector junction 104. Accordingly, in some instances the connector junction 104 is positioned at the proximal end 118.

As indicated above, the connector junction 104 is configured to facilitate communication between the component 120 of the intravascular device 100 and another, external device. More specifically, in some embodiments the connector junction 104 is configured to facilitate communication of data obtained by the component 120 to another device, such as a computing device or processor. Accordingly, in some embodiments the connector junction 104 is an electrical connector junction. In such instances, the connector junction 104 provides an electrical connection to the one or more electrical conductors 156, 157, 158 that extend along the length of the flexible elongate member 102 and are electrically coupled to the component 120. In other embodiments, the connector junction 104 is an optical connector. In such instances, the connector junction 104 provides an optical connection to one or more optical communication pathways (e.g., fiber optic cable) that extend along the length of the flexible elongate member 102 and are optically coupled to the component 120. Further, in some embodiments the connector junction 104 provides both electrical and optical connections to both electrical conductor(s) and optical communication pathway(s) coupled to the component 120. In that regard, it should again be noted that component 120 is comprised of a plurality of elements in some instances. In some instances, the connector junction 104 is configured to provide a physical connection to another device, either directly or indirectly.

As shown in FIG. 1, the cable 106 extends from the connector junction 104 to the connector 108. The connector 108 is configured to provide an electrical optical connection from the intravascular device 100 to additional processing or control systems. These may include, for example, computer systems that may be carried on portable computer systems or surgical consoles configured to process data detected or captured by the intravascular device 100 and to control the intravascular device 100. Some embodiments include a transmitter or transceiver in the connector junction 104 that facilitate wireless communication between the intravascular device 100 and another external device. Generally, any current or future developed wireless protocol(s) may be utilized. In yet other instances, the connector 110 facilitates both physical and wireless connection to another external device.

FIGS. 4-9 show the connector junction 104 in greater detail. FIGS. 5-7 show the connection junction 104 in longitudinal cross-section. FIGS. 8 and 9 show transverse cross-sections of the connector junction 104 taken along lines 8-8 and 9-9 respectively in FIG. 4. As can be seen in FIGS. 4-7, the connector junction 104 includes a grippable body 202 as a housing formed of a distal nose 204 and a proximal shell 206. Disposed within the connector junction 104, the connection junction includes a circuit board 209 that electrically connects to the electrical conductors 156, 157, 158 in the flexible elongate member 102 and to additional conductors in the cable 106. The circuit board 209 could be replaced with an optical connector as discussed above. However, for ease of explanation, this description will refer to the circuit board 209. The cable 106 may include one or more electrical conductors 182, 183, 184 that may receive signals from the circuit board 209 and carry signals to the connector 108 (FIG. 1).

The distal nose 204 includes a distal cylindrical portion 208, a tapered portion 210, and a proximal cylindrical portion 212. The distal nose 204 also includes a proximal end 216 (shown in FIGS. 5-7). The proximal end 216 includes a body portion 217 having an annular groove 218 formed therein for receiving a portion of the proximal shell 206. This annular groove 218 is best seen in FIG. 9, showing the annular groove 218 with a leading portion of the proximal shell 206 disposed therein.

The proximal end 118 of the flexible elongate member 102 extends into the distal cylindrical portion 208 toward proximal cylindrical portion 212. As can be seen in FIGS. 5-7 and 9, the distal nose 204 includes a hollow region 214. The trifilar 155 formed by the conductors extend through the hollow region 214 and onto the circuit board 209. Still referring to FIG. 9, the body portion 217 of the distal nose 204 also includes grooves 215 extending radially outwardly from an inner surface of the hollow region 214. The grooves 215 receive and securely hold the circuit board 209. Accordingly, the circuit board 209 is securely and immovably maintained in the distal nose 204 when the connector junction 104 is in its assembled state. Although shown with a taper and with cylindrical portion, other proximal shell embodiments include a different exterior profile.

The proximal shell 206 is formed with an open distal end 220 and a closed proximal end 222. The proximal shell 206 is sized to be easily grasped by a user, and in this embodiment, includes a diameter in the range of about 0.2 inch to about 1.5 inch. Accordingly, a user may easily grasp the proximal shell 206 so that the connection junction 104 may be used as a hand torque device in the manner described below. Other sizes are also contemplated. In this embodiment, the proximal shell 206 is formed with a textured outer surface that will enable additional friction enhancement for a comfortable and secure grip. In this embodiment, the textured outer surface is formed of a non-slip rubber with raised or recessed divots, other embodiments are formed of other materials or include alternative textured surfaces. The proximal shell 206 includes a hollow region 224 formed therein accessed through the open distal end 220.

With reference to the cross-sectional views in FIGS. 5-7, the open distal end 220 is sized to fit within the annular groove 218 in the distal nose 204 to form the graspable body 202. In some embodiments, the open distal end 220 fits via an interference fit, while in other embodiments, the open distal end 220 of the proximal shell 206 is inserted into the annular groove 218 of the distal nose 204 and secured in place via an adhesive, projecting or interference tabs, threads, or other connecting structure. Together, the hollow region 214 of the distal nose 204 and the hollow region 224 of the proximal shell 206 combine to form a connector chamber 230, containing the circuit board 209. As can be seen in FIG. 8, the proximal shell 206 includes grooves 221 extending radially outwardly from the hollow region 224. Like the grooves 215 in the distal nose 204, the grooves 221 in the proximal shell 206 receive and securely hold the circuit board 209. Accordingly, the circuit board 209 is securely and immovably maintained in the distal nose 204 and in the proximal shell 206 when the connector junction 104 is in its assembled state. The cable 106 extends through an opening in the closed proximal end 222 of the proximal shell 206 and the conductors 182, 183, 184 connect to the circuit board 209.

The circuit board 209 includes opposing first and second surfaces 302, 304, (shown in FIG. 6), with the first surface 302 including a plurality of distal connector terminals 308 and a plurality of proximal connector terminals (shown in FIG. 5). As can be seen in FIGS. 5-6, the trifilar 155 including the three leads or connectors 156, 157, 158 extend from the flexible elongate member 102 and are electrically connected to the circuit board 209 at the plurality of distal connector terminals 308. Likewise, the three exemplary connectors 182, 183, 184 in the cable 106 are electrically connected to the circuit board 209 at the plurality of proximal connector terminals 310.

In some embodiments, the circuit board 209 includes conductive traces or other circuitry. In some embodiments, the circuit board 209 includes components such as capacitors, resistors, or other components embedded in or attached to the circuit board 209. The circuit board 209 is configured to be attached to or secured in place in one or both of the distal nose 204 and the proximal shell 206. As described above, the circuit board 209 may be introduced into one of the hollow regions 214, 224 of the distal nose 204 and the proximal shell 206 and maintained in place within the hollow regions by the structure of the distal nose 204 and the proximal shell 206. In other embodiments, a compliant or rigid filler may be used to secure the circuit board 209 in place.

As best seen in FIG. 6, the distal nose 204 includes a slack chamber 250 in communication with the open proximal end 216. The slack chamber 250 may form a part of the hollow region 214 and may have a height greater than the thickness of the circuit board 209 and is sized and arranged to accommodate slack of the trifilar 155 formed of the conductors 156, 157, 158. In some embodiments, the trifilar 155 or the conductors 156, 157, 158 are coiled to create slack so that when the flexible elongate member 102 is bent, the conductors 156, 157, 158 are less likely to break. In addition, since the slack is accommodated within the slack chamber 250, as the flexible elongate member 102 flexes, the slack may be increased or decreased without invoking additional stress at the distal connector terminals 308.

In this embodiment, the core wire 166 also extends from the proximal end 118 of the flexible elongate member 102, extends through the slack chamber 250, and connects to the second surface 304 of the circuit board 209. FIG. 7 shows a view facing toward the second surface 304. In some embodiments, the core wire 166 connects to a terminal of the circuit board 209. In this embodiment, the core wire 166 is soldered to the circuit board 209 in a manner securing it in place. Here, the circuit board 209 is centrally disposed within the distal nose 204 and therefore, the core wire 166 is bent as it exits the flexible elongate member 102 to extend toward the second surface 304 of the circuit board 209, as shown in FIG. 6.

As can be seen in FIG. 6, since the core wire 166 does not include slack and since the electrical conductors 156, 157, 158 do include slack, the electrical conductors 156, 157, 158 have an axial length greater than the distance between the proximal end 118 of the flexible elongate member 102 and the distal edge of the circuit board 209, while the core wire 166 has an axial length substantially equal to the distance between the proximal end 118 of the flexible elongate member 102 and the distal edge of the circuit board 209.

In some embodiments, the slack in the conductors 156, 157, 158 is coiled, while in other embodiments, the slack is a partial coil and has waves or is otherwise curved to accommodate the excess length. In some embodiments, the slack is formed with slack length in the range of about 5-50 mm. In other embodiments, the slack is the range of about 5-25 mm. Yet, other lengths of slack are contemplated so long as the slack is sufficient to eliminate additional stress on the connections when the flexible elongate member is bent.

In accordance with the description above, the intravascular device 100 may be manufactured or assembled by providing the flexible elongate member 102 described above for introduction into vasculature of a patient. The flexible elongate member 102 includes the core wire 166 and one or more conductors 156, 157, 158, with the conductors 156, 157, 158 extending along the core wire 166. The conductors connect with the component 120 disposed at the distal portion 112 of the flexible elongate member 102 and extends from the proximal end 118. The proximal end 118 of the flexible elongate member 102 is introduced into the connector junction 104 by being disposed within the distal nose 204. In some embodiments, the proximal end 118 of the flexible elongate member 102 is introduced into the distal side of the distal nose 204, and then secured in place on the distal nose 204 using an adhesive, spot or laser welding, or using other methods.

With the conductors extending into the slack chamber 250, the circuit board 209 may be introduced to either the distal nose 204 or the proximal shell 206 and secured in place. It may be secured in place by being introduced into the grooves 215, 221 or other formed features in the distal nose 204 or the proximal shell 206. The conductors 156, 157, 158 are then electrically connected to terminals 308 on the circuit board 209. In some embodiments, the conductors 156, 157, 158 are soldered to the terminals 308 to create an electrical connection. In other embodiments, the conductors 156, 157, 158 are connected via a pin connection or other connection. The connector junction 104 may then be rotated and the core wire 166 may be soldered to the circuit board 209. In some embodiments, the core wire 166 is connected to the circuit board 209 before the electrical conductors 156, 157, 158. As such, the core wire 166 may help hold the circuit board 209 in place as the conductors are attached.

Prior to or after connecting the conductors 156, 157, 158 to the circuit board 209, the conductors may be coiled or looped or otherwise compressed to create slack in the conductors between the proximal end 118 of the flexible elongate member 102 and the terminals 308 on the circuit board 209. This slack may be accommodated in the slack chamber 250. The slack chamber 250 is sized to accommodate coils or loops or bends in the conductors formed by the slack. It is large enough to allow the slack to be increased or decreased as the flexible elongate member 102 is introduced into a patient's vasculature.

In some embodiments, the cable 106 is introduced into the proximal end 222 of the proximal shell 204 so that it projects out of the open distal end 220 of the proximal shell 206. The cable conductors 182, 183, 184 are then connected to the proximal terminals 310 on the circuit board 209 via soldering or other connection. With the conductors 182, 183, 184 attached to the circuit board 209, the proximal shell 206 may be advanced over the cable 106 so that the circuit board 209 enters into the hollow region 224. Ultimately, the proximal shell 206 may be introduced into the open end of the distal nose 204 to seal the circuit board 209 within the connector chamber 224 formed by both the distal nose 204 and the proximal shell 206. With the distal end 220 of the proximal shell 206 disposed within the proximal end 216 of the distal nose 204, the connection junction 104 may be sealed by securing the proximal end of the distal nose 204 to the proximal shell 206. This may be done using an adhesive, welding, threading, or using other methods.

Since the distal nose 204 and the proximal shell 206 are configured to securely maintain the circuit board 209 in place relative to the flexible elongate member 102, the terminals on the circuit board 209 do not rotate relative to the flexible elongate member 102 even when torque is applied to the connection junction 104.

It is worth noting that the order of assembly may differ from that described above. For example, in some embodiments, assembly includes attaching the conductors to the terminals before either of the distal nose and the proximal shell is placed about the circuit board 209. In addition, in some embodiments the circuit board is introduced into the proximal shell before introducing the circuit board to the distal nose. Other methods are also contemplated.

FIGS. 10 and 11 show another embodiment of a connection junction, referenced herein by the numeral 400, that may be used to form a part of the intravascular device 100 described above. In this embodiment, since the intravascular device 100 is a probe and, due to the permanently connected connector junction 104, cannot be used as a guidewire, the connection junction 400 includes a system for permanently removing the connector junction from a portion of the flexible elongate member. The remaining flexible elongate member may then be used as a guidewire. Accordingly, a health care provider may perform diagnostics testing, and then if desired, may permanently remove the connection junction by severing the flexible elongate member, and then may use they remaining flexible elongate member to guide a catheter or other medical instruction over the remaining portion of the flexible elongate member.

The connector junction 400 may include all the same features as the connection junction 104 described above, and they will not all be repeated here. Referring to FIGS. 10 and 11, the connector junction 400 includes a distal nose 402 and a proximal shell 406. In this embodiment however, the distal nose 402 includes an integrated cutting tool 410 that may be used to cut the flexible elongate member 102 from the distal nose 402 so other devices, such as balloon catheters for example, can be used over the remaining flexible elongate member. Once the flexible elongate member 102 is cut, it may no longer be used to measure physiological information of the patient. Here, the cutting tool 410 comprises a first arm 420 and a second arm 422 extending in the distal direction of the distal nose 402. The arms 420, 422 are formed substantially identically to one another, and extend on opposing sides of the elongated flexible member 102 protruding from the distal nose 402. Each of the arms 420, 422 includes a cutting tooth 426, such as a cutting blade, that together form cutting jaws 430.

The first arm 420 includes a region 432 having a first smaller thickness that may accommodate flexing under a load applied transverse to the direction of the arm 420. The arm 420 includes a distal region 434 having a second greater thickness that may be used to provide additional rigidity where the main load will be applied to cut through the flexible elongate member 102, including the core wire and the conductors in the flexible elongate member 102. In this embodiment, the distal region 434 is formed with a curved or rounded backing, although other shapes may be used. In this embodiment, the shape may be comfortable for the health care provider who may cut the flexible elongated member 102 by squeezing the two arms 420, 422 together between his fingers. The second arm 422 likewise includes a region 442 and a distal region 444 where the region 442 has a thickness less than a thickness of the distal region 444.

In the exemplary embodiment shown, the flexible arms 420, 422 extend in the distal direction from the distal nose 402. They extend from a connection location 448 that is proximal of the tip of the distal nose 402. Accordingly, the axial distance from the teeth 426 to a distal tip 450 of the distal nose 402 is d1, while the distance from the distal tip 450 of the distal nose 402 to the connection location 448 of the arms with the distal nose 402 is d2, where d2 is greater than d1. This ensures that while the arms 420, 422 have a length sufficient to provide suitable leverage and flexibility to be flexibly deformed or to elastically flex, the teeth 426 will still be maintained close to the distal tip 450, which holds or supports the flexible elongate member 102. In addition, each arm 420, 422 includes an aperture 454 formed therein. Here, the aperture 454 is aligned with the distal tip 450 of the distal nose 402 so that as the arms 420, 422 are deflected so that the teeth 426 cut through the flexible elongate member 102, the distal tip 450 may be received in the aperture 454, enabling the arms 420, 422 to flex further before the distal tip 450 causes interference. This allows the teeth 426 to be close together even in the neutral position shown in FIGS. 8 and 9. Accordingly, the cutting tool 410 may be made small and unobtrusive.

In the embodiment shown, the aperture 454 is formed as a rectangle, but the aperture may be any desirable shape. The cutting tool 410 may be formed of any flexible material and in some embodiments is formed of a polymer and is configured to elastically flex to cut the flexible elongate member 102. The teeth 426 may be formed of a suitable sharpenable material, and in some embodiments is formed of a metal material, such as stainless steel, titanium or other materials.

In use, a health care provider may perform a diagnostic angiography or treat a medical condition of a patient by feeding the flexible elongate member 102 into a patient's vasculature, such as a vessel to be monitored, using methods known in the art. The flexible elongate member 102 is then guided through the blood vessels until the component 120 is in the area to be studied. As the flexible elongate member 102 is introduced into the patient, the health care provider may grasp the connector junction 104 and rotate the flexible elongate member 102 within the vasculature by applying torque on the connector junction 104. This enables the health care provider to steer the flexible elongate member 102 through the vasculature. Since the connector junction 104 is non-rotatably fixed to the flexible elongate member 102, the health care provider can direct the flexible elongate member as desired. With the component 120 located in the desired location, and even as the flexible elongate member 102 is advanced into the vasculature, the component 120 may obtain physiological information relating to the condition of the patient. For example the component 120 may be a pressure transducer configured to detect pressure in the vasculature. The detected information may be sent as signals from the component through the conductors to the circuit board 209. Depending on the embodiment, the circuit board 209 may process the signal and then communicate additional signals over the cable 106 or may pass the signals directly through the circuit board 209 to the cable 106, and ultimately to a separate system for processing.

If the embodiment including the cutting tool 410 is used, after obtaining the desired information from the component 120, the surgeon may optionally decide to use the flexible elongate member 102 as a guidewire. To do this, the surgeon severs the flexible elongate member 102 to separate the connector junction 104 from the rest of the flexible elongate member. To do this, the surgeon may simply squeeze down on the cutting tool 410 to sever the flexible elongate member 102. This may be done by squeezing the arms together until the teeth 426 engage with and sever the flexible elongate member 102. Because of its proximity to the teeth 426, the distal end 450 of the distal nose 402 securely maintains the flexible elongate member 102 in a position between the teeth 426. As the arms 420, 422 are squeezed together, a portion of the distal nose 402 may be accommodated in the apertures 454 formed in the arms. This enables the arms 420, 422 to be squeezed without interference from the distal end 450 of the distal nose 402.

The intravascular device may be used in a region where physiological condition may be measured. In some examples, the intravascular devices described herein may be used to measure pressure or physiological condition in peripheral arteries of the leg, the aorta, kidneys, etc. It could be used in conjunction of a catheter to measure pressure and provide a higher fidelity pressure signal than that from a pressure transducer that measures through a lumen of a catheter. For example, the intravascular device 100 could be placed down the distal lumen of a pulmonary artery catheter to measure pulmonary artery pressure.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular probe comprising:
 a flexible elongate member configured to be introduced into vasculature of a patient, the flexible elongate member having a proximal portion and a distal portion, the distal portion including a component thereon configured to detect a physiological condition of a patient when the flexible elongate member is in a vasculature of the patient, the flexible elongate member comprising a core wire and a communication pathway extending at least partially along the core wire, the communication pathway being in communication with the component and extending to the proximal portion;
 a communication element configured to communicate signals representative of the detected physiological condition to a system; and
 a connector junction non-rotatably and permanently secured to the proximal portion of the flexible elongate member, the connector junction being sized for grasping by a health care provider and for rotation to rotate the flexible elongate member when the flexible elongate member is in a vasculature of the patient, the connector junction connecting the communication pathway in the flexible elongate member to the communication element to convey signals relating to the detected physiological condition to a system.

2. The intravascular probe of claim 1, wherein the connector junction comprises a chamber configured to accommodate flexing of the communication pathway as slack in the communication pathway.

3. The intravascular probe of claim 2, wherein the communication pathway comprises a loop as the slack in the communication pathway, the loop being disposed in the chamber.

4. The intravascular probe of claim 1, wherein the connector junction includes a connector chamber and a circuit board disposed in the connector chamber, the communication pathway being in communication with the circuit board.

5. The intravascular probe of claim 1, wherein the communication element is a cable extending from the connector junction.

6. The intravascular probe of claim 5, wherein the cable terminates at an electrical connector disposed at a proximal end of the cable.

7. The intravascular probe of claim 6, wherein the connector junction is disposed distal of the electrical connector and the cable.

8. The intravascular probe of claim 1, wherein the communication pathway comprises at least three separate signal carrying wires.

9. The intravascular probe of claim 1, wherein the housing is bonded to the proximal portion of the flexible elongate member with an adhesive.

10. The intravascular probe of claim 1, wherein the component is a pressure sensor.

11. The intravascular probe of claim 1, wherein the flexible elongate member comprises a first coil disposed distal of the components and comprises a second coil disposed proximal of the component, the first and second distal coils providing rigidity to the distal portion of the flexible elongate member.

12. The intravascular probe of claim 1, wherein the flexible elongate member comprises component housing, the component being disposed in the component housing.

13. The intravascular probe of claim 1, wherein the distal portion has a diameter of less than about 0.37 mm.

14. The intravascular probe of claim 1, further comprising a cutting tool on the connector junction configured to permanently sever the flexible elongate member for removal of the connector junction in a manner that a balloon or stent catheter may be introduced to vasculature over the remaining flexible elongate portion.

15. The intravascular probe of claim 1, wherein the flexible elongate member has a length between about 1300 and 4000 mm.

16. The intravascular probe of claim 1, further comprising a cutting tool on the connector junction configured to permanently sever the flexible elongate member for removal of the connector junction in a manner that a balloon or stent catheter may be introduced to vasculature over a remaining flexible elongate portion.

17. A method, comprising:

providing a flexible elongate member configured to be introduced into vasculature of a patient, the flexible elongate member having a proximal portion and a distal portion, the distal portion including a component thereon configured to detect a physiological condition of a patient when the flexible elongate member is in a vasculature of the patient, the flexible elongate member comprising a core wire and a communication pathway extending at least partially along the core wire, the communication pathway being in communication with the component and extending to the proximal portion;

connecting the connector junction to the communication pathway; and permanently affixing a connector junction to the proximal portion of the flexible elongate member, the connector junction being sized for grasping by a health care provider and for rotation to rotate the flexible elongate member when the flexible elongate member is in a vasculature of the patient.

18. The method of claim 17, further comprising creating slack in the communication pathway to accommodate tension on the communication pathway applied as a result of inserting the flexible elongate member through tortious vasculature.

19. The method of claim 18, further comprising looping the communication pathway to create the slack.

20. The method of claim 17, further comprising forming a first coil distal of the component of the flexible elongate member and forming a second coil proximal of the component of the flexible elongate member.

21. The method of claim 17, further comprising using the connector junction as a torque device during a medical procedure.

22. The method of claim 17, wherein the communication pathway comprises a conductor, and wherein connecting the connector junction includes soldering the conductor to circuitry maintained in the connector junction.

* * * * *